United States Patent [19]

Kitta et al.

[11] Patent Number: 4,678,338
[45] Date of Patent: Jul. 7, 1987

[54] COLOR SENSOR

[75] Inventors: Kenichi Kitta, Tokyo; Yasunori Kanazawa, Hachioji; Yoshiro Otomo, Mitaka, all of Japan

[73] Assignee: Hitachi Maxell, Ltd., Osaka, Japan

[21] Appl. No.: 554,363

[22] Filed: Nov. 22, 1983

[30] Foreign Application Priority Data

| Nov. 22, 1982 | [JP] | Japan | 57-203762 |
| Nov. 22, 1982 | [JP] | Japan | 57-203763 |
| Nov. 27, 1982 | [JP] | Japan | 57-206856 |
| Nov. 27, 1982 | [JP] | Japan | 57-206857 |

[51] Int. Cl.$^4$ ............................................. G01J 3/50
[52] U.S. Cl. ................................. 356/402; 356/420; 250/226
[58] Field of Search ............ 356/41, 44, 402, 406, 356/407, 409, 410, 411, 414, 420, 425, 40, 446; 250/564, 565, 226; 209/577, 580, 581, 582

[56] References Cited

U.S. PATENT DOCUMENTS

| 3,449,053 | 6/1969 | Cannady et al. | 356/407 |
| 3,593,055 | 7/1971 | Geusic et al. | 250/458.1 |
| 3,609,044 | 9/1971 | Murphy | 356/446 |
| 3,709,615 | 1/1973 | Blakeslee et al. | 356/225 |
| 3,725,701 | 4/1973 | Link | 250/343 |
| 3,910,701 | 10/1975 | Henderson et al. | 356/39 |
| 3,942,185 | 3/1976 | Lebailly | 250/226 |
| 3,986,777 | 10/1976 | Roll | 250/226 |
| 3,994,590 | 11/1976 | Di Martini et al. | 356/409 |
| 4,232,971 | 11/1980 | Suga | 356/402 |
| 4,241,738 | 12/1980 | Lubbers et al. | 356/40 |
| 4,278,349 | 7/1981 | Sander | 356/44 |
| 4,476,982 | 10/1984 | Paddock et al. | 356/406 |
| 4,494,875 | 1/1985 | Schramm et al. | 356/402 |

FOREIGN PATENT DOCUMENTS

| 2116386 | 10/1972 | Fed. Rep. of Germany | 356/420 |
| 0016826 | 2/1981 | Japan | 356/402 |
| 0012352 | 1/1982 | Japan | 356/446 |
| 1410823 | 10/1975 | United Kingdom | 356/402 |

OTHER PUBLICATIONS

"An On-Line Shade Monitor for Strip Materials," Purll et al., *Optica Acta*, v. 25, No. 12, Dec. 1978, p. 1197.

*Primary Examiner*—F. L. Evans
*Attorney, Agent, or Firm*—Birch, Stewart, Kolasch & Birch

[57] ABSTRACT

A color sensor includes a plurality of light emitting source of different colors each of which is driven in a time divisional manner to emit the different colors sequentially, a light receiving element for receiving the light from an object illuminated by the respective color lights from the light emitting sources and a circuit arrangement for producing output signals representing the color of the object.

10 Claims, 11 Drawing Figures

COLOR SENSOR

FIELD OF THE INVENTION

The present invention relates to a color sensor for recognizing the hue of articles by sensing rays of light passed through or reflected from the articles.

BACKGROUND OF THE INVENTION

In order to identify a desired kind of articles when among various other kinds of articles in a manufacturing process, it is well known to use a method of identifying the hue or color of the articles or objects.

FIG. 1 shows an example of a conventional color sensor for recoginizing color of articles. Referring to FIG. 1, rays of white light are emitted from a light source 1 made of a tungsten lamp and a portion of the rays of light is reflected by a half mirror 2. The light reflected by the half mirror 2 is collimated by a lens 3 at a position at which an article or an object to be recognized is placed. Each of the objects has identifying a specific color given to it either by the color of the material forming the object or by a label or mark attached on the surface of the object. The light reflected by the object is changed into a parallel light by the lens 3 and is received by a photo sensing unit 6 after passing through the half mirror 2 and a color filter 5. The color filter 5 has a specific spectral characteristic of transparency corresponding to the desired hue or color of the object sought so as to allow the light of the color of the object sought to pass through the filter. The output signal of the photo sensing unit 6 is amplified by an amplifier 7 and in turn applied to a comparator 8. The output signal of the amplifier 7 is compared with a reference voltage applied to the one input terminal of the comparator 8. The comparator produces a digital signal (e) that is a high level output (referred to as 1 hereinafter) or a low level output (referred to as 0 hereinafter) depending on whether or not the output level of the amplifier 7 exceeds the reference voltage. The contents of the digital signal (e) i.e., 1 or 0 represent whether or not the photo sensing unit 6 receives the reflected light, accordingly the content of the digital signal (e) represents the hue of the object.

FIG. 2 is another example of a conventional color sensor and the reference numerals 9 and 10 show optical fibers respectively. In FIG. 2 like parts in FIG. 1 are designated by the same reference numerals. In this conventional color sensor, a light emitting diode is used as the light source 1 and the light of the light source 1 is projected on the object 4 through the optical fiber 9. The light reflected by the object 4 is passed through the optical fiber 10 and received by the photo sensing unit 6.

According to the color sensor shown in FIG. 2, the light source is a light having the same color as the desired color so that the filter 5 provided in the color sensor in FIG. 1 can be omitted and the area of the light emitting port of the optical fiber can be minimized and furthermore the light emitting port can be placed at very near the object so that the radius of spot light incident to the object can be minimized, thereby reducing the total size of the color sensor per se as compared to the color sensor shown in FIG. 1 and enabling the recognition of the color of smaller sized objects.

However, the conventional color sensors as described above are not capable of recognizing three or more colors because the recognizable color in the conventional color sensors is limited by the color of the filter 5, or the color of the light emitting diode 1. For example, when a red color filter or a red light emitting diode is used, the color sensor can recognize only whether the color of the object is red or not.

One way of recognizing more than three colors of the objects is to provide an arrangement for interchanging a plurality of filters of various kinds of colors in place of the color filter 5 in FIG. 1. For example, assuming that objects each having one of at least four different color groups such as red, green, yellow and a group consisting of all other colors are to be classified, red objects are classified using a red filter, subsequently green objects are classified using the green filter. The same operation is performed using the yellow filter and the remaining color filter to classify the yellow objects and other color objects are left undetected so that the objects can be classified into four color groups.

This method, however, requires to the repetition of the identifying means for each of the colors corresponding to the number of the kinds of the interchangeable color filters. Accordingly it takes much time and work to classify the color of the objects, and it further requires updating the reference voltage of the comparator 8 each time the color filters are interchanged.

Another method of classifying the color of the objects having more that three colors is to provide a plurality of color sensors for each of the colors to be classified. For example, if there are four colors to be classified, four color sensors each having a different color filter are employed. This method is effective to decrease the time for classifying the objects into four colors by placing each of the color sensors along the line of flow of the objects. However, the number of color sensors used increases as the number of the colors to be classified increases. Furthermore, in order to recognize the various colors correctly, the respective color sensors must have a uniform sensing characteristics. If there is dispersion of the color sensing characteristics among the respective color sensors due to the difference of the brightness of the light sources, the difference of the color filtering characteristics and/or the difference of the sensitivity of the respective photo sensing units, setting of the reference voltage of the respective comparators of the color sensors is very difficult.

SUMMARY OF THE INVENTION

An essential object of the present invention is to provide a color sensor which is able to recognize more than three kinds of colors or hues with a simple construction and with an easy adjustment of the various parts of the color sensors.

According to the present invention there is provided a color sensor including a plurality of light emitting sources, each being capable of emitting different color lights respectively for driving said light sources in a time divisional manner so as to emit said different color lights in time sequentially one after another; sequentially projecting the emitted different color lights onto an object, the color of which is to be sensed; light receiving means for receiving the lights reflected from or passed through the object and producing output signals representing the value of the lights from the object corresponding to each of the different color lights; and circuit means for recognizing the color of the object by the output signals of the light receiving means.

DETAILED DESCRIPTION OF THE PREFERRED EMBODIMENTS

Figure 3:
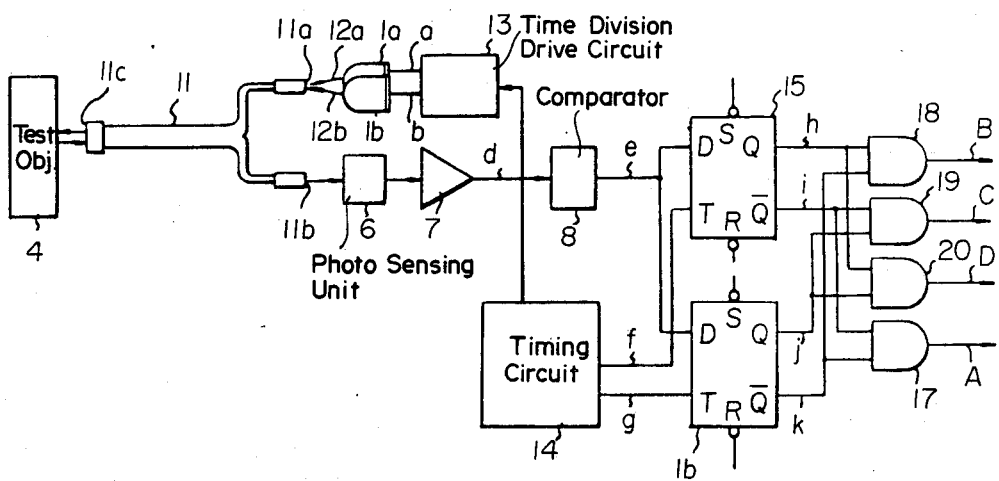
FIG. 3 is a schematic diagram showing one example of an embodiment of a color sensor according to the present invention.
Figure 5:
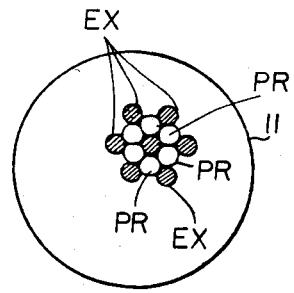
FIG. 5 is a front view showing a way of distributing the optical fibers of a light transferring path used in the embodiment shown in FIG. 3.

Referring now to FIG. 3 there are provided two light emitting sources $1a$, $1b$ using light emitting diodes of different colors such as red and green, each of the light emitting sources $1a$ and $1b$ is driven to emit the red light and the green light alternately by a time divisional drive circuit 13 in a time divisional manner. A light transmission path 11 is formed by a plurality of optical fibers bundled together with a part of the one end of bundled optical fibers of the light transmission path 11 opposed adjacent to the light emitting sources $1a$ and $1b$ to form a light entrance $11a$ to which the light from the light emitting sources $1a$ and $1b$ is enters and the remaining part of the said one end of the optical fibers opposed to the photo receiving unit 6 to form a light exit $11b$ to project the light reflected from the object 4 on the photo sensing unit 6. The other ends of the part of the optical fibers forming the light entrance $11a$ are disposed to face the object 4 to form the light exit $11c$ of light to project the light of the light emitting sources $1a$ and $1b$ on the object 4. The other ends of the remaining part of the optical fibers forming the light exit $11b$ for the photo sensing unit 6 are disposed to face the object 4 to form the light entrance $11c$ for receiving the light reflected from the object 4. At the end, $11c$, of the light transmission path 11, the respective optical fibers EX for receiving the light and the optical fibers PR for projecting the light are distributed alternately as shown in FIG. 5 to receive or project the light uniformly over the entire area of the end, $11c$.

The photo sensing unit 6 is formed by a single photo transistor to produce an analog signal corresponding to the quantity of the incident light to the photo transistor.

The comparator 8 is applied with a reference voltage at one of the input terminals and compares the analog signal applied to another input terminal from the amplifier 7 with the reference voltage to provide an output of 1 or 0 depending on whether or not the analog signal exceeds the reference voltage.

Two flip-flops 15 and 16 of D type receive the output of the comparator 8, i.e. the digital signal e to hold thereof at the timing when every strobe pulses f, g are applied. The flip-flops 15 and 16 form a signal holding circuit.

AND gates 17, 18, 19 and 20 form a logic circuit to calculate a logic of recognizing the colors of the object on the basis of the level of the digital signal e held in the hold circuit.

Figure 4:
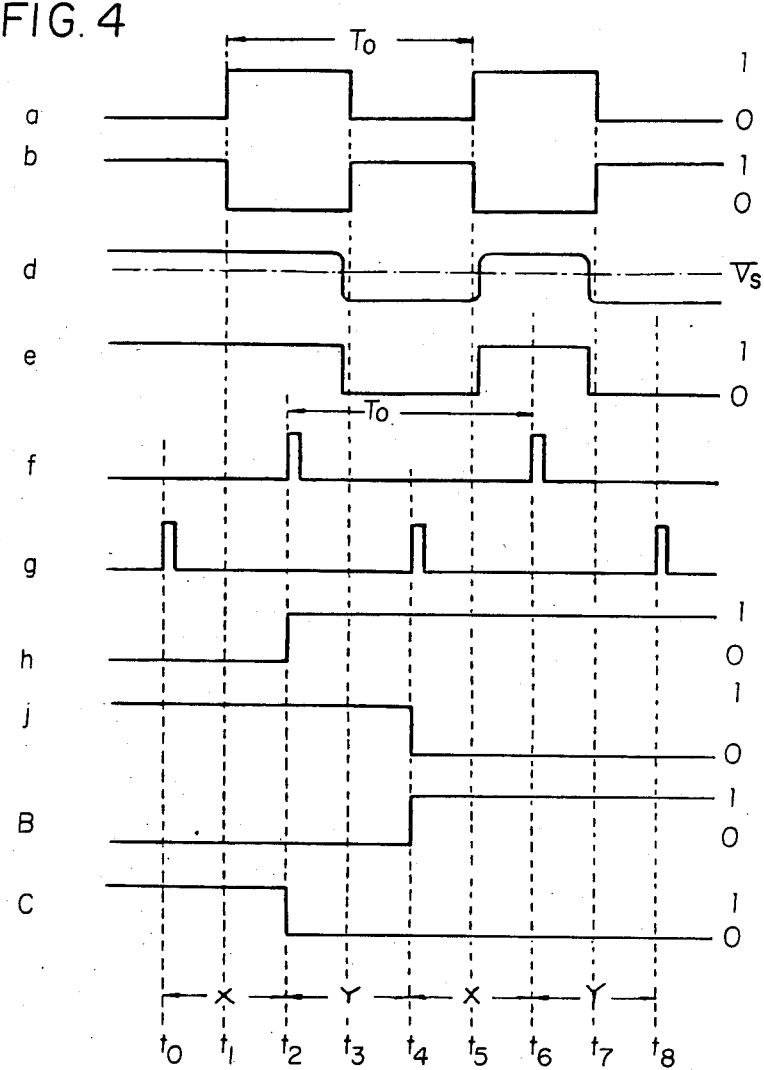
FIG. 4 is a schematic diagram showing wave forms of the essential portion of the color sensor shown in FIG. 3.

Referring to FIGS. 3 and 4, a timing circuit 14 supplies timing signals to the time divisional drive circuit 13, which produces drive current a and b to drive the light emitting sources $1a$ and $1b$ with a phase difference of 180° and period of To with a duty ratio of 50%.

By this arrangement the light emitting sources $1a$ and $1b$ emit the red light and the green light alternately, whereby the red light and the green light are projected on the object 4 in a time divisional manner passing through the entrance $11a$ and the light transmission path 11. It is to be noted that the periods during which the light emitting source $1a$ emits the light are designated by $t_1$ through $t_3$ and $t_5$ through $t_7$, and the period during which the light emitting souce $1b$ emits the light is designated by $t_3$ through $t_5$.

The object 4, illuminated, reflects the light of a color corresponding to the color of the surface of the object and the reflected light passes the exit $11c$ and the light transmission path 11 and is received by the photo sensing unit 6, which produces an analog signal of a large amplitude when the reflected light is received. As a shown in FIG. 4 assuming that the object 4 having red color is illuminated from the timing $t_1$, the amplitude of the analog signal of the output of the photo sensing unit 6 becomes large in the time periods $t_1$ through $t_3$ and $t_5$ through $t_7$ during which the light emitting source $1a$ emits the light because the red object 4 reflects the red light and absorbs the green light, and the amplitude becomes small in the period $t_3$ through $t_5$ during which the light emitting source $1b$ emits the light.

The analog signal from the photo sensing unit 6 is amplified by the amplifier 7 to produce the analog signal d of the predetermined amplitude and is fed to the comparator 8 to be compared with the reference voltage Vs. The comparator 8 produces the digital signals e, the level of which is 1 in the periods $t_1$ through $t_3$ and $t_5$ through $t_7$ during which the amplitude of the analog signal is large, and is 0 in the period $t_3$ through $t_5$ during which the amplitude of the analog signal is small.

The digital signals produced by the comparator 8 are fed to the D input terminals of the flip-flops 15 and 16 which receive the strobe pulses f and g at the T input terminals from the timing pulse generator 14. The D type flip-flop 15 holds the level of the digital signal e at the time of the positive edge of each of the strobe pulses f and the D type flip-flop 16 holds the level of the digital signal e at the positive edges of each of the strobe pulses g. By this operation, the output of the D type flip-flop 15 becomes 1 upon receipt of the strobe pulse f at the timing $t_2$ in the periods of $t_1$ through $t_3$ thereby the Q output thereof being 1 with the $\overline{Q}$ output being 0. The 1 level of the Q output of the flip-flop 15 shows the object 4 has red color and the 1 level is held by the next positive edge of the strobe pulse f.

Since the digital signal e in the period $t_3$ through $t_5$ is 0, the Q output of the D type flip-flop 16 becomes 0 upon receipt of the positive edge of the strobe pulse g at the timing $t_4$ in the period $t_3$ through $t_5$ with the $\overline{Q}$ output of thereof being 1. The 0 level of the D type flip-flop 16 shows that the photo sensing unit 6 does not receive the green light and the 0 level is held until the next strobe pulse g is applied.

The table 1 shows the relation of the output of flip-flops 15 and 16 and the absense or presence of the light of the respective colors incident to the photo sensing unit 6.

The AND gates 17, 18, 19 and 20 judge the states of the flip-flops 15 and 16 to generate signals representing the hue of the objects. As shown in FIG. 3, the AND gate 18 receives the output signals h and k, the AND gate 19 receives the output signals i and j, and the AND gate 17 receives the output signals i and k.

Although the timings of the light emission by the light emitting sources 1a and 1b are shifted by $T_o/2$ each other, as the timings of the strobe pulses f and g are also shifted by $T_o/2$ and the state of the output of the D type flip-flop 15 can be held until the other flip-flop 16 reads in the output of the comparator 8 upon receipt of the strobe pulse g, the AND gates 17 through 20 receive the signals h, i, j, and k simultaneously. In FIG. 4 Y is the period for holding the output of the comparator 8 and X is the period for judging the state of the output of the flip-flops.

The relationship between the color of the object and the states A, B, C and D of the outputs of the AND gates 17, 18, 19 and 20 is shown in the table 2. As understood from the table 2, when the color of the object is red, only the output B of the AND gate 18 is 1 with the remaining outputs A, C and D being 0. In the table 2, the term "other color" means a color other than red, green, white and yellow.

According to the first embodiment of the color sensor according to the present invention, the four kinds of hues can be recognized or classified by using only two color light emitting sources and the recognition of the hue can be made in the real time basis. In this embodiment, the currents of the light emitting diodes 1a and 1b are so adjusted that the intensity of the lights of the light emitting diodes 1a and 1b is equal. Thus if the color of the objects is yellow, the quantity of the red light and green light reflected from the object 4 and received by the photo sensing unit 6 is lower than quantity of the reflected light of the object having red or green, eventually the output amplitude of the amplifier 7 for the yellow object is smaller than that for the red or green object. Thus, the reference voltage of the comparator 8 is set to recognize the yellow by setting the reference voltage in such a manner that the comparator 8 generates 1 in both cases when the red light is illuminated and when the green light is illuminated.

Since the red light and the green light are emitted in a time divisional manner, only one comparator 8 is necessary for digitizing the analog signal fed from the amplifier or the photo receiving unit 6, so that only one reference voltage must be used for the both of the red and green lights, thereby facilitating adjustment of the reference voltage without consideration about the balance of the reference voltage for each of colors.

Figure 1:
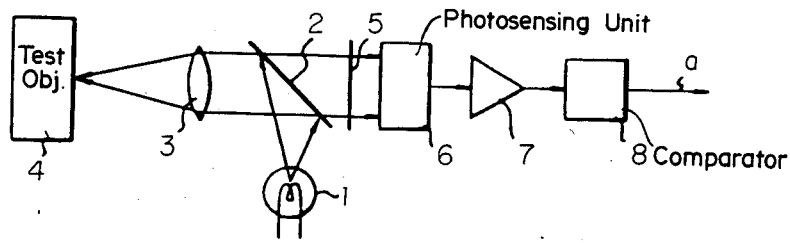
FIG. 1 is a schematic diagram showing one example of a conventional color sensor.
Figure 2:
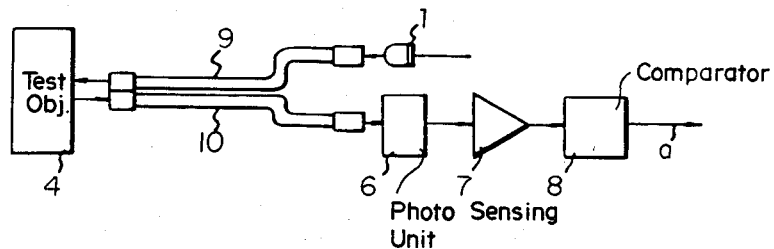
FIG. 2 is another example of a conventional color sensor.

It is not essential to use a light transmission path but the path can be two separate paths 9 and 10 as shown in FIG. 2 one for illuminating the light on the object and another for receiving the reflected light from the object.

Figure 6:
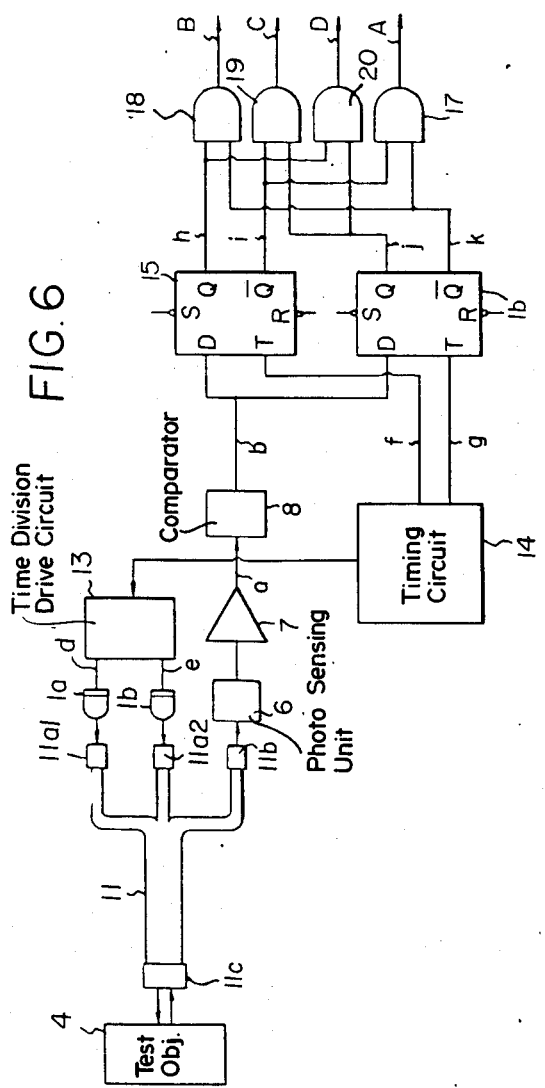
FIG. 6 is a further example of the color sensor according to the present invention.

FIG. 6 shows the second embodiment of the color sensor according to the present invention wherein the light entrance 11a of the light transmission path 11 is divided into two light entrances 11a1 and 11a2 by dividing the bundled optical fibers two groups. The light entrance 11a1 is disposed to face adjacent to the red light emitting source 1a and the light entrance 11a2 is disposed to face to the green light source 1b.

Figure 7:
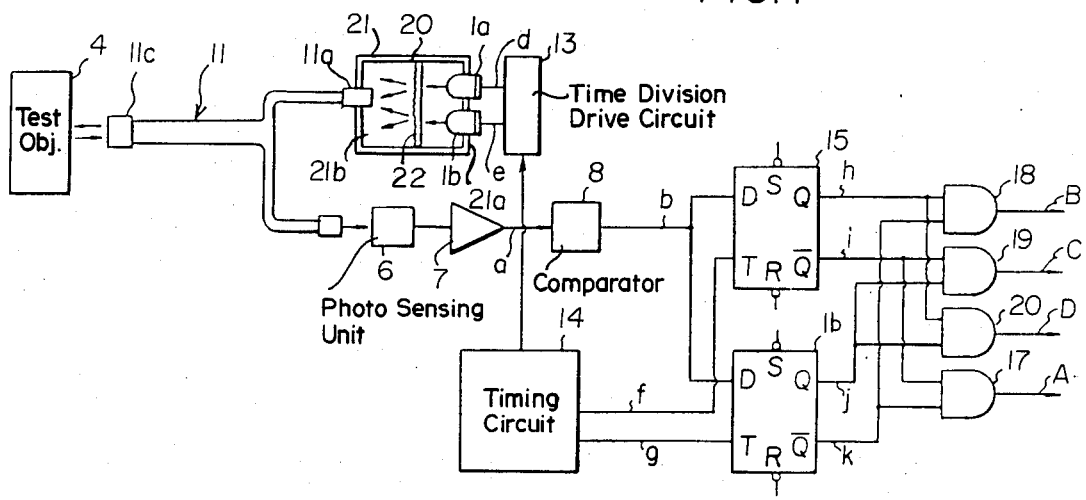
FIG. 7 is a schematic diagram showing a still further example of the color sensor according to the present invention.

FIG. 7 shows the third embodiment of the color sensor according to the present invention wherein the light entrance 11a of the color sensor shown in FIG. 3 is connected with a light emitting unit 20 having a box-like enclosure 21 made of an opaque material. The light emitting source 1a and 1b are respectively fixed to one face 21a of the enclosure 21 with the light emitting faces of the light emitting sources 1a and 1b directed to the opposite face 21b on which the light entrance 11a of the light transmission path 11 is connected. The enclosure 21 is separated by a light diffuser 22 such as a sheet of frosted glass disposed between the both faces 21a and 21b. By this arrangement, the light emitted from the light emitting source 1a and/or 1b is diffused by the light diffuser 22 and in turn the diffused light enters the light entrance 11a. By using the light diffuser 22, directionality of the light emitting sources such as light emitting diodes can be broadened so that the intensity of the light entering the light entrance 11a from both of the light emitting sources 1a and 1b becomes uniform. The color recognition operation is similar to the arrangement shown in FIG. 3.

Figure 8:
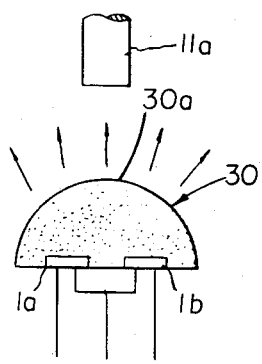
FIG. 8 is a cross sectional view of an example of light emitting unit used in the color sensor according to the present invention.

In order to broaden the directionality of the light emitting diodes 1a and 1b, hemispherical enclosure 30 may be used as shown in FIG. 8. In this embodiment, the light emitting diodes 1a and 1b are mounted on the flat face of the enclosure 30 which is filled with a light diffusing material. The light entrance 11a of the light transmission path 11 is disposed to oppose the apex 30a of the hemispherical portion of the enclosure 30.

Figure 9:
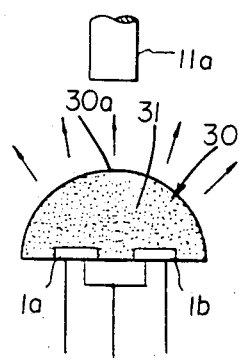
FIGS. 9 and 10 are schematic diagram showing still further modification of the light emitting units used in the color sensor according to the present invention.

As the light emitting diodes, GaAlAs diode 1a for the red light and GaAs:Si diode 1b for the infra red light may be used. For the light diffusing material, as shown in FIG. 9, anti-Stokes fluorescent material 31 may be filled in the enclosure uniformly, so that green light may be emitted by the infra red light emitted from the light source 1b. Although the shape of the enclosure is not limited to the hemispherical shape, in the case of the hemispherical shape the, quantity of the light entering the light transmision path may be increased.

Figure 10:
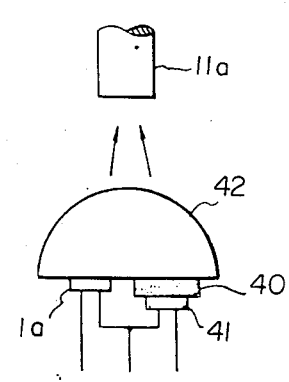

Another modification of the light emitting unit is shown in FIG. 10, wherein a layer 40 made of anti-Stokes fluorescent material is interposed between the GaAs:Si diode 41 and the flat face of a hemispherical enclosure 42 made of transparent material.

The Ga AS:Si diode 41, the layer 40 and the flat face of the enclosure 42 may be adhered integrally. The enclosure 42 acts as a lens to collimate both of the lights from the diodes 1a and 41 to the light entrance 11a.

Figure 11:
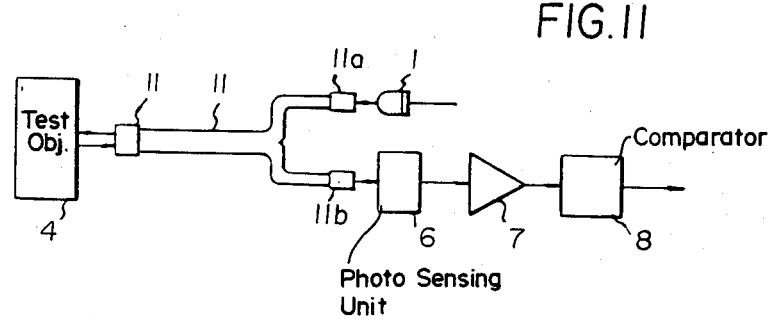
FIG. 11 is a schematic diagram showing an example of a color sensor having one colored light emitting source using a light transferring path with one end portion formed as shown in FIG. 5.

The bundled optical fibers with the end portions PR and EX thereof so uniformly distributed as shown in FIG. 5 may be used for the color sensor having one color light emitting source 1 as shown in FIG. 11.

Although the embodiments of the color sensor described above are provided with two light emitting sources of different colors, the number of the colors of the light emitting source is not limited to two but n kinds of color light sources may be used to recognize $2^n$ kinds of colored objects.

TABLE 1

| States of flip-flops | | Q | Q̄ | Photo sensing unit 6 |
|---|---|---|---|---|
| D type flip-flops 15 | "1" | 1 | 0 | red light is present |
|  | "0" | 0 | 1 | red light is absent |
| D type flip-flops 16 | "1" | 1 | 0 | green light is present |
|  | "0" | 0 | 1 | green light is absent |

TABLE 2

| State of flip-flop 15 | State of flip-flop 16 | output of AND gates | | | | hue of the object |
|---|---|---|---|---|---|---|
|  |  | A | B | C | D |  |
| 0 | 0 | 1 | 0 | 0 | 0 | other color |
| 1 | 0 | 0 | 1 | 0 | 0 | red |
| 0 | 1 | 0 | 0 | 1 | 0 | yellow |
| 1 | 1 | 0 | 0 | 0 | 1 | yellow & white |

What is claimed is:

1. A color sensor for recognizing the relative color of an object comprising:
   first illumination means for supplying light of a first wavelength to said object;
   second illumination means for supplying light of a second wavelength different from said first wavelength to said object;
   means for monitoring said light of said first and second wavelengths from said object, and means for monitoring including,
   a single photosensor producing an output indicative of the quantity of light received from said object, and
   comparator means for comparing the output of said single photosensor to a reference value, the output of said comparator being a logical one when light supplied said photosensor exceeds said reference value and being otherwise a logical zero;
   timing control means for generating first and second alternate enable signals to enable said first and second illumination means, alternately; and
   hue determination means, operatively connected to said timing control means, for retaining the logical values developed by said comparator means, said hue determination means receiving first and second phase shifted latch timing signals developed by said timing control means to reset said hue determination means, said hue determination means developing at least three logical outputs, each representative of the presence or absence of a different color of said object.

2. The color sensor of claim 1 wherein said hue determination means develops four outputs representative of four colors.

3. The color sensor of claim 2 wherein said four colors include red, green, yellow and another color.

4. The color sensor of claim 1 further comprising light transferring means for providing light from said first and second illumination means to said object and from said object to said means for monitoring.

5. The color sensor of claim 4 wherein said light transferring means comprises:
   a plurality of optical fibers bundled together with a portion of said bundle of said optical fibers having a first end at a first light receiving point facing said first and second illumination means to form a first light entrance for receiving light from said first and second illumination means and the remaining portion of said bundle of the optical fibers having a first end facing said means for monitoring to form a first light exit to the means for monitoring; a second end of the bundle of said optical fibers facing said object to form a second light entrance for receiving the light from the object and a second light exit for projecting the light on the object.

6. The color sensor according to claim 5, wherein the second end of said bundled optical fibers is so formed that each of the optical fibers forming the second light entrance and the second light exit is distributed to receive the light from the object and to project the light to the object uniformly over the entire area of the second end of the bundled optical fibers.

7. The color sensor according to claim 4, wherein the first and second illumination means are mounted on one wall member of an enclosure with said light transferring means mounted on an opposing wall member of said enclosure, said enclosure being provided with light diffusing means disposed between said first and second illumination means sources and said light transferring means.

8. The color sensor according to claim 7, wherein said enclosure is a box.

9. The color sensor according to claim 4, wherein the first and second illumination means are mounted on a flat wall member of an enclosure with the light emitting portion of the first and second illumination means directed to a wall member of the enclosure to which a light entrance of said light transferring means is faced, said enclosure is of a hemispherical shape with the inside filled with a light diffusing material.

10. The color sensor according to claim 7 wherein said light diffusing means is a fluorescent material and the respective first and second illumination means are light emitting diodes of different colors, one of said light emitting diodes being an infra red light emitting diode.

* * * * *